(12) United States Patent
Holler

(10) Patent No.: US 8,377,652 B2
(45) Date of Patent: Feb. 19, 2013

(54) **PRODUCTION OF LONG CHAIN UNBRANCHED BETA-POLY(L-MALIC ACID) BY LARGE SCALE *PHYSARUM* CULTIVATION AND HIGH-GRADE PURIFICATION OF THE SAME**

(75) Inventor: Eggehard Holler, Bad Abbach (DE)

(73) Assignee: Arrogene Nanotechnology, Inc., Los Angeles, CA (US)

( * ) Notice: Subject to any disclaimer, the term of this patent is extended or adjusted under 35 U.S.C. 154(b) by 490 days.

(21) Appl. No.: 12/390,507

(22) Filed: Feb. 23, 2009

(65) Prior Publication Data

US 2010/0216199 A1 Aug. 26, 2010

(51) Int. Cl.
*C12P 21/06* (2006.01)
(52) U.S. Cl. ...................................................... 435/69.1
(58) Field of Classification Search ................... 435/69.1
See application file for complete search history.

(56) References Cited

PUBLICATIONS

Ljubimova et al. Jan. 30, 2008, available online Feb. 8, 2007; Nanoconjugate based on polymalic for tumor targeting. Chemico-Biological Interactions 171(2): 195-203.*

* cited by examiner

*Primary Examiner* — Karen Cochrane Carlson
(74) *Attorney, Agent, or Firm* — Volpe and Koenig, P.C.

(57) ABSTRACT

The invention is a large-scale production and purification of beta-poly(L-malic acid), biodegradable natural polyester of L-malic acid of molecular weight 30,000 to 300,000 from plasmodia of the Physarum family, especially Physarum polycephalum. This will replace previous laborious and uncontrolled production by bioreactor methods of high productivity and quality, especially to obtain pure polymer of high molecular weight. The described 20-liter bioreactor method can be scaled up for industrial purpose at optimal production and minimum growth time to prevent degradation The invention includes the method of isolation of polymalic acid of 100,000 Mn (number-averaged molecular weight) from the culture broth optimized towards high yields of extremely pure polymalic acid. The non-hygroscopic, water and organic solvent-soluble polymer is endotoxin and agglutinin free and ready to use in chemical syntheses. Because of its high molecular weight and purity it offers a wide spectrum of applications in pharmacy and medicine.

14 Claims, 3 Drawing Sheets

Fig. 2

| Strain | Color (genotype) | $10^{-12}$ g polymalic acid per nucleus | $10^{-6}$ g polymalic acid per g plasmodium | g secreted polymalic acid per hour and g plasmodium |
|---|---|---|---|---|
| MC3CVII | Yellow (whiA+/whiA+) | 2.0 ± 0.5 | 60 ± 15 | 200 |
| CH813 x LU861 | Yellow (whiA+/whiA+) | 1.1 ± 0.3 | 460 ± 90 | More than 400 |
| LU688 | Yellow (whiA+) | 3.6 ± 1.0 | 1000 ± 200 | 200 |
| OX110 x RA271 | Yellow (whiA1/whiA+) | 0.9 ± 0.3 | 47 ± 15 | 20 |
| LU897 x LU898 | White (whiA1/whiA1) | 1.5 ± 0.4 | Not detectable | Not detectable |
| LU887 | White (whiA1) | 1.1 ± 0.3 | Not detectable | Not detectable |

PRODUCTION OF LONG CHAIN UNBRANCHED BETA-POLY(L-MALIC ACID) BY LARGE SCALE *PHYSARUM* CULTIVATION AND HIGH-GRADE PURIFICATION OF THE SAME

AREA OF THE ART

The current invention is in the area of fermentation microbiology and especially the production and of high molecular weight (50,000 to 100,000) unbranched β-Poly(L-malic acid) by plasmodia of the Physarum family through fermentation of D-glucose and carbond dioxide, and of its subsequent high-grade purification.

BACKGROUND OF THE INVENTION AND DESCRIPTION OF THE PRIOR ART

Unbranched Poly(β-L-malic acid) (PMLA) in FIG. 1 is a biopolymer produced from renewable feedstocks (1). The polymer consist of units L-malic acid esterified via the carboxylic group in beta-position and the hydroxyl group. PMLA can also be synthesized chemically (1); however, chemically synthesized PMLA shows lower purity and partial racemisation. The molecular weight ($M_n$, number-averaged molecular weight) of the biopolymer ranges from 3,000 to 300,000 with the highest proportion at 50,000-100,000 (2). Plasmodia of the Physarum family produce PMLA in excess of their physiological needs and secrete large amounts into the culture medium (3). Published producers for the strains M3CII and M3CVIII (ATCC 204388 and ATCC 96951) of Physarum polycephalum have been reported by us, but any other Physarum species can be active in PMLA production as claimed here [see references in (1)]. The yield by conventional production methods in culture flasks is less than 1 g/liter of culture broth.

Some filamentous fungi produce short-chain PMLA (branched and of approximately 10,000 molecular weight) that is conjugated to poly(glucan) [(4) and references in (1)] involving activities of secreted enzymes to remove PMLA from the poly-glucan residues (1). This kind of PMLA preparation cannot be purified to chemical homogeneity because of uncontrolled amounts of covalently attached sugar moieties.

PMLA from plasmodia is unbranched, devoid of any covalently attached other molecule, and easily purified to chemical homogeneity. Physarum produces agglutinins of low molecular mass. These secreted proteins purify by a characteristic pathway that is different from the one used for the purification of polymalic acid. PMLA preparations contain endotoxin originating from yeast extract included in the fermentation broth. The contaminant has not been removed.

Polymalic acid is produced by the species of the Physarum family, in particularly by the yellow strains of Physarum polycephalum, and secreted into the culture broth. The broth will contain then small amounts of peptides/proteins, polysaccharides (slime), pigments, and various inorganic salts (1) that must be removed by purification.

The polymer consists of units malic acid esterified between their hydroxyl group and the carboxylic group in β-position (FIG. 1). The carboxyl groups in α-position are free to ionize with a pKa of about 4 to yield polyanion at neutral pH. The acid form and the anionic form of PMLA differ by solubility in organic solvents. Both forms are highly soluble in water, but only the acidic form dissolves in acetone and several other organic solvents.

The polyanion is precipitated with ethanol, especially in its form of the calcium salt. PMLA binds with high affinity to polycationic (chromatographical) material from which it is eluted with queopus solutions containing >0.5 M NaCl or any other cation.

The binding of the polyanion to polycationic material, the solubility of PMLA in the acid form in acetone, and the ready precipitation of the calcium salt with ethanol allow the efficient isolation of highly purified polymalic acid after conversion of the calcium-salt into PMLA-acid.

PMLA in the culture broth has a molecular weight 30,000 to 300,000 and the inhomogeneity corresponds to a polydispersity value ($M_w/M_n$) of 2 (1). PMLA of a narrow distribution in molecular weight can be produced by gel permeation chromatography.

Because of the instability of the ester bond, exposure to solutions of pH<5 and pH>9 must be avoided to keep spontaneous hydrolytic cleavage at a minimum (7). PMLA is also enzymatically hydrolysed in the culture broth at a maximal rate when pH is 3-4 (9).

Polymalate Producing Organisms (FIG. 2)

Polymalate is produced by plasmodia of the Physarum family. Plasmodia of the Physarum family are multinuclear, large, at a late growth stage slimy, unicellular organisms, commonly called slime molds (5). Plasmodia of Physarum polycephalum and of other family members convert D-glucose to PMLA (6). Several Physarum strains have been shown to secrete PMLA into the culture broth. Among these are strains M3CVII and M3CVIII. To date all yellow colored strains tested were found to be good PMLA producers (FIG. 2), and it is evident that all yellow strains are good producers of this polymer. It is proposed to generate new such strains of the Physarum family and of other myxomyceteae strains by cross breeding and selection for PMLA synthesis following an automated chemical testing of the culture broth (1). Viable plasmodia can be stored in the form of resting cells, so-called spherules, which are the dormant and highly durable during may years (1). Spherules can be prepared and activated to plasmodia by following existing methods.

Prior Art PMLA Culture Methods

For simple PMLA production, shaken cultures in 2 liter indented Erlenmeyer flasks of 300 mL production medium are inoculated with 5 ml cells of a starting culture. After four days at 24° C. in the dark, the culture broth is removed and is processed for the isolation of the polymer.

The PMLA production medium contains the following ingredients (g/liter):

10 D-glucose
10 Bactotrypton (DIFCO, Germany)
1.5 yeast extract (DIFCO)
3.5 citric acid monohydrate
2.0 $KH_2PO_4$
0.6 $MgSO_4$-heptahydrate
0.085 $MnCl_2$-tetrahydrate
0.085 $FeSO_4$-hepthydrate
0.035 $ZnSO_4$-heptahydrate
0.0025 hemin
Deionized water to make.

Solutions in the absence of D-glucose and hemin are brought to pH 4.3 with 5 M NaOH and are then sterilized (autoclaved) at 120° C. The remaining ingredients at 10 times concentration are sterilized separately at 120° C. and then added to the other ones. Maintenance culture are routinely grown for 2 days at 24° C. in 100 ml medium (500 ml indented flasks).

Precultures (for inoculation) and production cultures are grown in the same medium at the same conditions.

Spherules

Spherules is a durable resting stage cell form of the plasmodium and can be kept for many years on filter strips without loosing viability. A piece of filter paper containing sperules (e.g. strain M3CVII) can be placed onto a 1.5% agar (10 cm petri dish) containing 2-fold diluted culture medium (for microplasmodia, see below) and left at 24° C. in the dark. After 2-3 days, plasmodia start to hatch. A growing plasmodium (a flat cell) is then transferred to fresh agar and grown until it almost completely covers the agar surface. The cell is detached from the agar and transferred into 100 ml culture medium (500 ml dented Erlenmeyer flask) and cultured at 24° C. in the dark on a Gyro-Shaker (G10 New Brunswick) at 100-180 rounds per minute (rpm) (plasmodia require lots of oxygen). For optimal culturing, every 2-3 days, a portion of 5-10 ml settled cells is transferred to fresh culture medium.

Spherules are prepared to have a reliable stock supply of plasmodia for future use. Spherules can be stored at a dry and cool place for many years. For their preparation, a 2-day-culture of microplasmodia is allowed to settle to the bottom of the flask. The supernatant is decanted quantitatively. One hundred milliliterts of spherulization medium is added and shaking continued at 24° C. After three to four days orange colored spherules are formed. They are centrifuged, resuspended in a small amount of spherulization medium and placed in small aliquots on sterile filter paper. After they have dried, they are stored at 4° C. in the refrigerator.

Spherulization Medium (g/liter):

| | |
|---|---|
| 4.0 | citric acid |
| 0.09 | $FeSO_4 \times 7H_2O$ |
| 0.6 | $MgSO_4 \times 7H2O$ |
| 1.2 | $CaCl_2 \times 2H_2O$ |
| 0.085 | $MnCl_2 \times 4H_2O$ |
| 0.035 | $ZnSO_4 \times 7H_2O$ |
| 4.4 | $KH_2PO_4$ |

The aqueous solution is adjusted with 30% KOH to pH 3.8 and sterilized for 20 min at 120° C.

Analytic methods for asseying PMLA (reference 2):

Hydroxamate/Fe(III)-color assay (For rapid, but less sensitive measurements):

Adjust the sample to 320 TI with distilled water and mix with 160 µl of reagent A. Add 160 µl of reagent B. Allow the reaction to proceed for 10-15 min. Mix with 160 µl of reagent C, and read the absorbance at 540 nm wavelength (1 mg/ml PMLA=2.5 $A_{540}$).

Reagent A=10% (w/v) hydroxylammonium chloride.
Reagent B=10% (w/v) NaOH.
Reagent C=5% (w/v) $Fe(III)Cl_3$ in 12% (v/v) HCl.

Malate dehydrogenase assay (For sensitive measurements):

Hydrolyze the sample PMLA for 2 h at 100° C. in the presence of 2 M $H_2SO_4$. After careful neutralization with 5 M NaOH, L-malate (besides a few percent fumaric acid) is measured photometrically at 340 nm wavelength in equivalents of NADH formed in the presence of 60 units/liter malate dehydrogenase in the presence of 40 mM $NAD^+$, 0.76 M glycine and 0.5M hydrazine hydrate (0.5 M), pH 9.0 for 30 min at 37° C. The absorbance of NADH is standardized by repeating the enzymatic reaction with known amounts of L-malate.

Enzymatic Test for Verification of the Linear Structure of PMLA

The unbranched nature of polymalic acid can be verified by its enzymatic exhaustive cleavage to L-malic acid by Polymalatase (14). PMLA with branching points or chain substitutions is not cleaved beyond cbranching points. Branching is experimentally detected by comparing the experimental content of malic acid, using any one of the quantitative malic acid detection assays, with the theoretical content of malic acid calculated on the basis of the sample weight.

Prior Art Poly(Malate) Isolation Technique

For purification, culture broth is passed through DEAE-Cellulose (8) followed by washing over a Büchner funnel with 15 volumes of 10 mM sodium phosphate buffer pH 7, containing 0.3 M NaCl that removes proteins and most of the polysaccharides and pigments. PMLA is eluted with 6 volumes of 10 mM sodium phosphate solution of pH 7 containing 0.7 M NaCl. After proper dilution, the polymer is adsorbed on fresh DEAE-cellulose material and subjected to chromatography with 7 volumes buffer containing a gradient of 0.2-1.5 M NaCl. This step is repeated, then the PMLA-containing fractions precipitated with 70% (v/v) ethanol in the presence of 0.2 M NaCl and concentrated by freeze-drying. Salt is completely removed by molecular sieving over a Sephadex G25 fine. PMLA, sodium salt, is converted into the acid form over Amberlite 120 $H^+$ then freeze-dried and dissolved in anhydrous acetone. Insoluble material is removed and acetone evaporated under reduced pressure to yield solid, highly purified, colorless PMLA-acid. The prepared material is not hygroscopic and shows crustallization. The yield is 20-30% of the amount of PMLA in the culture broth. The labor time is approximately 2 weeks.

Technical Problems Of The Prior Art PMLA Production And Isolation Methods

The prior production method suffers from low production capacity and bad reproducibility affording a high expenditure of labor, space, glass ware, and other materials, and is not applicable to biotechnology. Growth in 500 mL culture broth in indented Erlenmeyer flasks is not commercially realizable. Results of culturing on shaker tables are not reproducible because of uncontrolled pH, aeration, agitation and prolonged incubation. Multiple handling in the absence of sterilization results in frequent and high levels of contamination, or loss of culture and low PMLA production The production method has limited capacity not eceeding 10 liters of culture broth, allowing a maximum output of 2-3 g PMLA.

Purification leads to excess inorganic salt (NaCl, KCl, or $CaCl_2$) in polymalate preparations that must be totally removed by repeated gel filtration before acidification. Failure will provoke low quality of polymalic acid by containing HCl that will cause hygroscopicity and rapid degradation of the polymer. Extended exposure to DEAE-cellulose and Amberlite 120 $H^+$ leads also to cleavage and loss of high molecular weight PMLA. Preparations contained polypeptides such as endotoxins.

Objects of the invention

It is an object of the present invention to define reproducible conditions for a culture broth optimal for high molecular weight PMLA production;

It is a further object of the present invention to present al large scale production of PMLA allowing scale up PMLA production in closed bioreactors of virtually any size;

It is another object of the present invention to allow plasmodia cultivation under control and repeated adjustment of temperature, pH, aeration, agitation as well as suppression of foam and avoidance of contamination; and It is a still further object to establish perfect culture conditions that avoid cell death and physical cell lysis by providing unharsh conditions for growth and harvesting while reducing spontaneous and enzymatic cleavage of produced PMLA.

It is an additional object to provide a simplified isolation method on a large scale that can be readily scaled up;

A still further object of the invention is to increase capacity and throughput of the polymalic acid isolation method at a minimum of time;

Another object is to provide improved removal of salt from the polymalate preparation before conversion into polymalic acid over Amberlite 120 H+in order to avoid contaminatiin by HCl derived from salt; and An additional object of the present invention is to convert PMLA by removal of solvent water within a minimum of time to avoid HCl-catalysed degradation after acidification.

Another object of the present invention is to purify polymalic acid free of agglutinins and endotoxins.

SUMMARY OF THE INVENTION

By controlled growth in the bioreactor with shortend residence time, the amount and average size was of the polymer was greatly improved from prior less than 1 g/L to 3 g/L and a shift in mass of polymer from 30,000 to 50,000-100,000 Molecular weight.

The production was much lest cost intensive than the classical one using indented Erlenmeyers.

The yield and purity of polymalic acid was greately improved by involving rapid large-scale DEAE-chromatography and ethanol precipitation of the Ca-polymalic acid salt.

The content of endotoxins was reduced to undetectable levels.

DESCRIPTION OF THE FIGURES

FIG. 2, PMLA levels detected in several different strains of Physarum showing high PMLA in yellow strains.

DETAILED DESCRIPTION OF THE INVENTION

Figure 1:
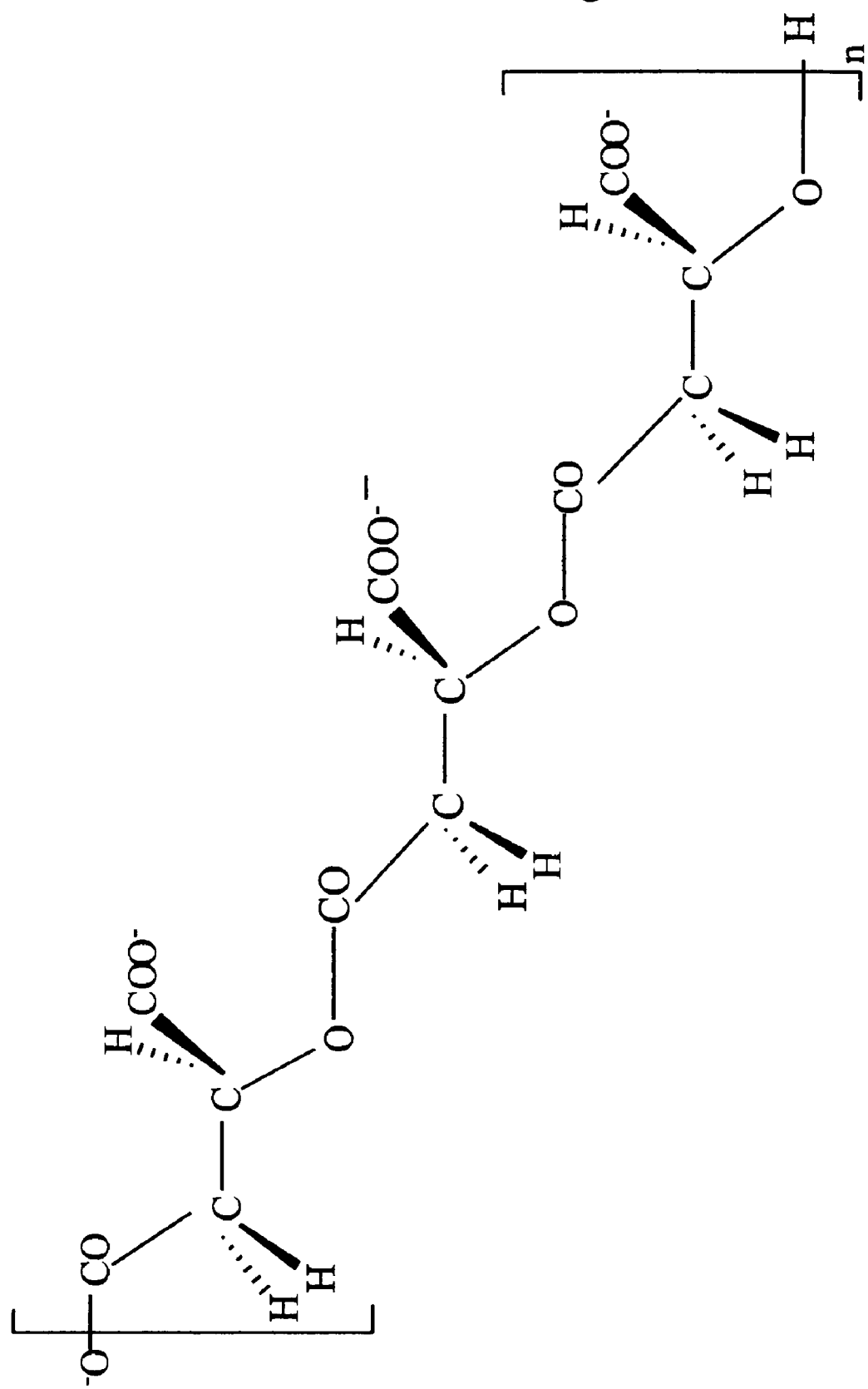
FIG. 1, formula of polymalate

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved method to produce and isolate polymalic acid.

Polymalate Production in a Closed Stainless Steal 20-liter Bioreactor

The following example of PMLA production is given for a 20-liter BIOSTAT® C Bioreactor from BRAUN BIOTECH INTERNATIONAL.

Inoculum:
1.5% (w/v) D-glucose
1% (w/v) Bactotrypton (DIFCO, Germany)
0.06% (w/v) $CaCl_2$
0.15% (w/v) yeast extract (DIFCO)
0.35 (w/v) citric acid monohydrate
0.2% (w/v) $KH_2PO_4$
0.06% (w/v) $MgSO_4$-heptahydrate
0.085 g/liter $MnCl_2$-tetrahydrate
0.085g/liter $FeSO_4$-hepthydrate
0.035 g/liter $ZnSO_4$-heptahydrate
0.0025 g/liter hemin
Deionized water (to make).

The solution without D-glucose and hemin is brought to pH 4.5 with 5 M NaOH and sterilized at 120° C. The remaining ingredients at a 10 fold higher concentration are sterilized separately at 120° C. and combined with the first solution. Six 1 liter aliquots of culture medium (each contained in a 5 liter Erlenmeyer flask) are each inoculated with 40 ml of settled bed plasmodia of any yellow strain Physarum polycephalum (e.g. strain M3CVII (AtCC204388) and then grown for 40 hours at 25° C. in the dark. The cells are allowed to settle.

The supernatant of settled cells must be clear. Otherwise, the flask contents are discarded. The settled cells are washed 3× with sterile salt solution containing 0.2% (w/v) $KH_2PO_4$, 0.35% (w/v) citric acid, 0.1% (w/v) $CaCl_2$, 0.085 g/liter $MnCl_2$-tetrahydrate, 0.085 g/liter $FeSO_4$-hepthydrate, and 0.035 g/liter $ZnSO_4$-heptahydrate.

Bioreactor Results

The bioreactor culture medium contained:
3% (w/v) D-glucose
1% (w/v) Bactotrypton (DIFCO, Germany)
0.25% (w/v) yeast extract (DIFCO)
0.06% (w/v) $CaCl_2$
0.35 (w/v) citric acid monohydrate
0.2% (w/v) $KH_2PO_4$
0.06% (w/v) $MgSO_4$-heptahydrate
0.085 g/liter $MnCl_2$-tetrahydrate
0.085g/liter $FeSO_4$-hepthydrate
0.035 g/liter $ZnSO_4$-heptahydrate
0.0025 g/liter hemin
Deionized water to make.

The solution was adjusted to pH 4.5 with 5 M NaOH, and 18 liters of the solution were sterilized in the bioreactor at 121° C. for 30 min at 1 bar. A sterile suspension of 45% (w/v) $CaCO_3$ and 10-fold concentration of a sterile solution of hemin were pumped into the bioreactor to give final concentrations of 3.5% (w/v) $CaCO_3$ and 0.0025 g/liter hemin. Because of the $CaCO_3$, the pH increased to pH 5.5. Pumping was continued, and 750 ml settled bed microplasmodia of the inoculation culture were added to the biorector under sterile conditions with the help of a type MCP ISMATEC® ISM 404 peristaltic pump with tubing of 6.4 mm diameter set at 69-80 rpm that corresponds to a flow rate of 300 ml/min.

The culturing of plasmodia was carried out for 75 h at 25° C. with a 10 liter/min air flow and 150 rpm constant stirring by a 3-leaf segment stirrer C20-2 (3 etages) BIOSTAt® by BRAUN BIOTECH INTERNATIONAL. A minimum amount of Sigma Antifoam A (A-5758) at a dilution of 1:30 (distilled water) was added as needed. The fermentation was terminated when the pH showed a plateau at pH 4.78-4.80 signifying the end of PMLA-production. PMLA content was then determined by the Hydroxamate/Fe(III)-color assay which indicated an $A_{540}$ reading of 1.0 for a 160 μl sample. At the end of the fermentation, the culture broth in the bioreactor was immediately cooled to 10° C. and adjusted to pH 7.5 by the addition of 2 M NaOH.

Features of the invented culture method:
The invention combines bioreactor technology with microbiological techniques with the aim of
polymalic acid production from Physarum polycephalum strain M3CVII (ATCC 204388);
an increase in capacity and ready to scale up;
sustainable instrumentation;

readily scalable methodology for carrying out PMLA production in stainless steel bioreactors;

optimization of production reproducibility and polymalate quality by control of fermentation conditions;

increased productivity for polymalic acid by supplying simultaneously D-glucose and $CaCO_3$;

Protection of high molecular weight polymalic acid by minimizing spontaneous hydrolytic chain scission through shortening the time of fermentation, lowering the pH of the culture broth to pH 5.5, and by rapid adjustment of the broth to pH 7.5 with 2 M NaOH with cooling to 10° C. during fermentation termination;

low enzymatic cleavage activity of polymalatase in the culture broth due to pH increased to pH 5.5 (away from enzyme optimum) and reduced polymalate production time from 96 hours to 75hrs;

high yield (20 g polymalate/18 liter bioreactor);

fixed working scheme and reproducible time schedule;

less laborious than previous methods and completion in less time;

controlled culturing in a closed reactor conditions reducing cell death under unfavorable culture conditions and contamination like in open culture vessels Isolation and Purification of Polymalic Acid and Its Salts:

Culture broth was adjusted to pH 7.5 with 2 M NaOH while cooled to 10° C., and plasmodia were allowed to settle by gravity. The broth was removed by passing over a cheese cloth or a similar filter device or by low speed centrifugation (500×g). The clear broth was then diluted 1:1 by volume with 0.05 M Tris-HCl pH 7.5 and pumped at a speed of 10 liter per hour in the reverse flow mode (i.e., from the bottom up) through Streamline-DEAE-cellulose (1.5 liter bed volume per 10 liter of culture broth in a column of a 12 cm diameter). The adsorbed PMLA was washed with 5 column volumes of 20 mM Tris-HCl buffer containing 0.2 M NaCl entering from the bottom of the column until all yellow pigment, sugars, proteins and nucleic acids (all by standard text book assays) had disappeared. PMLA was then eluted from the top of the column with 2-3 column volumes of 0.7 M NaCl in the same 20 mM Tris-HCl buffer pH 7.5.

A 5.0 M solution of $CaCl_2$ was stirred into the eluted fractions containing PMLA to give a final concentration of 0.1 M $CaCl_2$. Addition was followed by slow addition of non-expensive, ice-cold technical grade ethanol (96%) to give a final ethanol concentration of 70-80% (v/v). Precipitation was completed overnight at −20° C. The precipitated PMLA, Ca-salt, was harvested by centrifugation or filtration and washed with 2-3 volumes of 80% (v/v) ice-cold aqueous ethanol. At this stage, the material could be stored for several months at −20° C. without measurable loss of quality.

The precipitate was dissolved in a minimum of distilled water and processed further in either of the two following ways:

(a) Without further purification, the material was converted to PMLA-acid by passage over Amberlite 120 $H^+$. The resulting PMLA-acid was instantaneously freeze-dried and dissolved into water-free 1:1 (v/v) mixture of acetone and isobutylmethylketone. Insolubles were removed, and PMLA-acid was precipitated with diethylether. Any up to then resisting pigment remained in the mother liquor. The pure PMLA-acid is inhomogenous over a wide range of molecular weights.

(b) Crude fractionation according to molecular weight and removal of traces of pigment as well of residual inorganic salt was achieved by gel permeation chromatography on Sephadex-G25 fine grade (5×100 cm).

Figure 3:
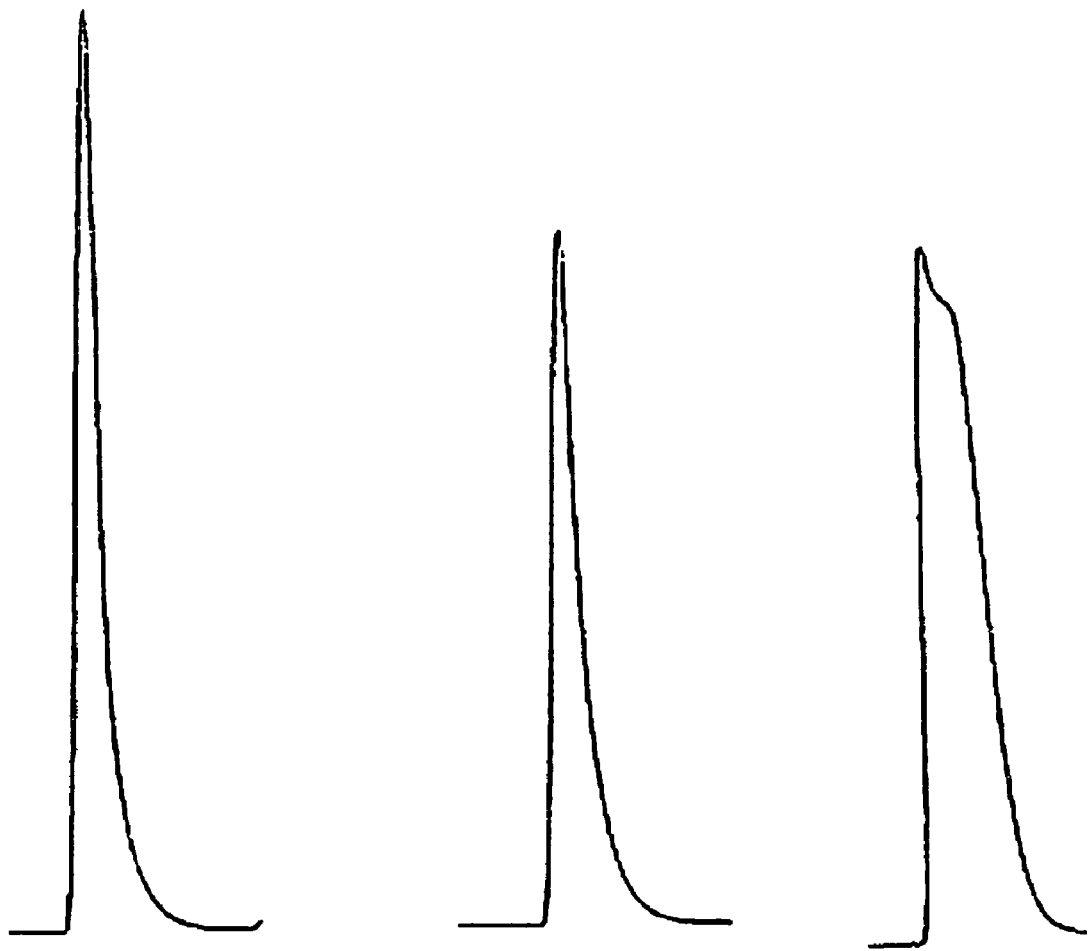
FIG. 3, molecular weight distribution after seize exclusion HPLC of PMLA-acid prepared from different fractions after sieving over Sephadex G25 and Amberlite 120 H$^+$ acidification according to method (b) for purification.

Fractionation resulted in three equally sized pools of molecular mass 60-300 kDa, 30-50 kDa, and 10-30 kDa. The fractions of each range were combined yielding preparations of polymalic acid: Mn 100000 (major fraction, typically 7-10 g), Mn 50000 (typically 5-8 g), Mn 15000.(typically 3-5 g). Mn denotes number-averaged molecular weight. Polydispersity factors were in the range 1.2-1.4. An example of there preparations is shown in FIG. 3. If endotoxin removal is desired, fractions were then diluted to 1 mg/mL PMLA in phosphate buffer (150 mL portions in 150 mM buffer, pH 6.8) and made 1% (v/v) in Triton X-114 before 5 min vigorous mixing. Mixtures were allowed to clear on ice and then incubated for 10 min under shaking at 37° C. After 5 min centrifugation at 5000×g, the upper layer was removed and concentrated by membrane filtration. Residual Triton was removed by gel filtration over PD-10 column (GE Healthcare) prewashed and eluted with LAL reagent water (Lonza). All fractions were then passed over Amberlite 120 $H^+$ (3×20 cm), immediately collected on ice, and polymalic acid instantaneously freeze-dried.

Method (b) is the preferred one, because it achieves substantial fractionation by size size being fast, reproducible, and convenient. The purities of polymalic acid obtained by either methods are similar. In either case, the prepared PMLA-acid was stored at −20 ° C. The overall labor time for the fermentative production and isolation of highly purified PMLA-acid from 20 liter culture broth was eight days. The yield of highly purified polymalic acid, Mn 100000, was 30-40% of polymalic acid in the culture broth. The kind of polymalic acid lost during purification was mainly of low molecular weight (<20,000).

Purity and Properties of the Isolated Polymalic Acid:

The preparations were of extreme purity as indicated by optical rotation (7, 10), absorbance—(7), infra red—(7), C13/H1—NMR-spectra (7,10,11), elementary analysis (7), melting analysis (11), and the ability of polymalic acid to crystallize [Ref. (1), and unpublished data]. According to the results of conventional tests, the preparations of polymalic acid with Mn 100,000 and with Mn 50,000 after endotoxin removal by the Triton method were devoid of endotoxins (<0.1 EU/mg by the LAL turbidity kinetic method) and of agglutinins, which do not copurify under the conditions of the purification methods.

Preparations of polymalic acid and polymalate are white, non-hygroscopic powders after lyophilisation. The acid tends to become crystalline when concentrated from a solution of anhydrous acetone. Polymalic acid and polymalate solubilize extremely well in water, the acid strongly acidifying the solution, the dissolved salt remaining neutral. Polymalic acid dissolved in water is spontaneously cleaved under acidic and basic conditions. The hydrolysis at neutral pH is almost completed after 24 hrs at room temperature, ultimately forming L-malic acid, while the salt is stable for several days at pH 7.0. Solutions should be kept at low temperature <0.4° C. or better frozen at <(−)20° C. in order to slow down cleavage. The lyophilized polymer salt and acid is substantially more stable and can be stored for any period at −20 to −80° C. The lyophilized salt (usually Ca or Na salt) of polymalic acid withstands transportation for several days to probably weeks at temperatures below 40° C.

The pendant carboxyl groups are chemically substituted after activation using carbodiimide derivatives (12). In these reactions, the main chain ester bonds remain intact if synthesis is carried out in anhydrous organic solvents. The carboxyl substitution may stabilize the main chain ester bond.

Features of the invented isolation method:

The invention is to combine several biotechniques to
increase the capacity to purify polymatae from the culto broth ready to be scaled up;
to employ sustainable instrumentation (regenerative and reusable chromatographic materials and columns, reusable setups of chromatographic columns, pumping devices, lyophilizer);
to achieve reproducible quality by following the purification via polymalic acid, not via the salt. Various salt forms of polymalate can then be obtained by neutralization of polymalic acid with appropriate metal hydroxide or carbonate;
by choosing ethanol precipitation of the polymer in the form of calcium-polymalate as an improved method;
precipitation being a robust method where technical ethanol is sufficient;
efficient and fast size fractionation using a large Sephadex G25 column;
high yields of polymalic acid Mn 100,000 in the order of 30-40%.
Achievement of high grade pure polymalic acid Mn 100,000.
Complete removal of contaminants. On demand, removal of endotoxin by the Triton method.

Uses of the Product

After isolation from the culture broth, polymalic acid and various salts are obtained with purity and stability superior to chemically synthesized polymalic acid. Because of the relative high costs of fermentation/purification, polymalaic acid has not been commercially available. A scale-up of the invented bioreactor production and invented purification protocol should allow industrial production and commercial availablility of polymalic acid and its salts. A variety of applications are possible. PMLA is non-toxic, non-immunogenic, and biodegradable. It has a high value for syntheses in chemistry, especially for pharmaceutical chemistry and nanochemistry (12, 13). Due to its biocompatibility and the high number of reactive carboxylic groups and their straight-forward chemistry, it offers an effective platform for covalent conjugation of a wide range of pharmaceutically active compounds, unmatched by any other polymers known to date having the high level of biocompatibility.

Polymalic acid is an optimal material to be used in many kinds of applications, due to its solubility in aqueous and organic solvents and its chemical ease for conjugation with interesting compounds especially by condensation reactions involving carbodiimide reagents. In addition, PMLA can be used as starting material for the design of micelles, microspheres, biocapsules, biogels, liquid crystals, and coat materials. On a larger scale, a field of application could be the use of (biodegradable) adhesives, plastics, dispersion media, packaging for controlled release, or for hydrophilic coating.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

References

1. B.-S. LEE, M. VERT, AND E. HOLLER (2002) IN BIOPOLYMERS (DOI, Y. AND STEINBÜCHEL, A., EDS.) PP 75-103, NEW YORK, WEINHEIM (BERGSTRASSE).
2. E. HOLLER AND B.-S. LEE (2002) RECENT RES. DEVEL. ANAL. CHEM. 2, 177-192.
3. A. SCHMIDT, C. WINDISCH, AND E. HOLLER. NUCLEAR ACCUMULATION AND HOMEOSTASIS OF THE UNUSUAL POLYMER B-POLY(L-MALATE) IN PLASMODIA OF PHYSARUM POLYCEPHALUM. EUR. J. BIOCHEM. 70, 373-380. 1996.
4. K. RATHBERGER, H. REISNER, B. H. WILLIBALD, H.-P. MOLITORIS, AND E. HOLLER. COMPARATIVE SYNTHESIS AND HYDROLYTIC DEGRADATION OF POLY(L-MALATE) BY MYXOMYCETES AND FUNGI. MYCOL. RES. 103, 513-520. 1999.
5. T. G. BURLAND, K. L. SOLNICA, J. BAILEY, D. B. CUNNINHAM, AND W. F. DOVE. PATTERNS OF INHERITANCE, DEVELOPMENT, AND MITOTIC CYCLE IN THE PROTIST PHYSARUM POLYCEPHALUM. ADV. MICROB. PHYSIOL 35, 1-69. 1993.
6. B.-S. LEE, T. MAURER, AND H. R. KALBITZER, E. H. POLY(B-L-MALATE) PRODUCTION BY PHYSARUM POLYCEPHALUM. 13C NUCLEAR MAGNETIC RESONANCE STUDIES. APPL. MICROBIOL. BIOTECHNOL. 52, 415-420. 1999.
7. H. FISCHER, S. ERDMANN, AND E. HOLLER. AN UNUSUAL POLYANION FROM PHYSARUM POLYCEPHALUM THAT INHIBITS HOMOLOGOUS DNA POLYMERASE ALPHA IN VITRO. BIOCHEMISTRY 28, 5219-5226. 1989.
8. E. HOLLER (1997) IN HANDBOOK OF ENGINEERING POLYMERIC MATERIALS (N. P. CHEREMISINOFF, ED.) PP 93-103, MARCEL DEKKER INC., NEW YORK.
9. C. KORHERR. M. ROTH. E. HOLLER. POLY(P-L-MALATE) HYDROLASE FROM PLASMODIA OF PHYSARUM POLYCEPHALUM. CAN. J. MICROBIOL. 41(SUPPL. 1), 192-199. 1995.
10. S. CAMMAS, P H. GUERIN, J P. GIRAULT, E. HOLLER, Y. GACHE. M. VERT. NATURAL POLY(L-MALIC ACID): NMR SHOWS A POLY(3-HYDROXY ACID)-TYPE STRUCTURE. MACROMOLUCULES 28, 4681-4684. 1993.
11. C. E. FERNANDEZ, M. MANCERA, E. HOLLER, J. BOU, J:A:GALBIS, S. MUNOZ-GUERRA. MACROMOL. BIOSCI. 5, 172-176. 2005, and: J. A. PORTILLA, M. GARCIA-ALVAREZ, A. MARTINEZ D. E. ILARDUYA, E. HOLLER, S. MUNOZ-GUERRA. NANOSTRUCTURED COMPLEXES OF POLY(β,L-MALATE) AND CATIONIC SURFACTANTS: SYNTHESIS, CHARACTERIZATION AND STRUCTURAL ASPECTS. submitted to MACROMOL. BIOSCI. 2005.
12. B. S. LEE, M. FUJITA, N. M. KHAZENZON, K. A. WAWROWSKY, S. WACHSMANN-HOGIU, D. L. FARKAS, K. L. BLACK, J. Y. LJUBIMOVA, E. HOLLER, POLYCEFIN, A NEW PROTOTYPE OF A MULTIFUNCTIONAL NANOCONJUGATE BASED ON POLY (β-L-MALIC ACID) FOR DRUG DELIVERY. BIOCONJUG CHEM. 17, 317-326, 2006.
13. J. A. PORTILLA, M. GARCIA-ALVAREU, A. M. DE ILARDUYA, E. HOLLER, S. MUNOZ-GUERRA, NANOSTRUCTURAL COMPLEXES OF POLY(BETA-L-MALATE) AND CATIONIC 45 SURFACTANTS:

SYNTHESIS, CHARACTERIZATION AND STRUCTURAL ASPECTS. BIOMACROMOLECULES 7, 161-170. 2006.

14 W. MUELLER, M. HAINDL, E. HOLLER, PHYSARUM POLYMALIC ACID HYDROLASE: RECOMBINANT EXPRESSION AND ENZYME ACTIVATION. BIOCHEM BIOPHYS RES COMMUN. 377, 735-40. 2008

What is claimed is:

1. A method for producing a polymalic acid (PMLA) comprising:
    culturing in a bioreactor plasmodia of a *Physarum polycephalum* strain that produces the PMLA under conditions suitable for decreasing spontaneous hydrolytic and enzymatic scission of a PMLA chain, wherein the strain is at least one strain selected from: MC3CVII, MCVIII, CH813xLU861, LU688, OX110xRA271, LU897xLU898 and LU887;
    isolating and purifying the PMLA from bioreactor culture broth;
    fractionating the PMLA according to molecular weight and collecting a plurality of molecular weight fractions of the PMLA, wherein each of the plurality of the molecular weight fractions is characterized by a molecular mass of 100,000 Da, or more.

2. The method according to claim 1, wherein the conditions comprise a time of culturing for 75 hours.

3. The method according to claim 1, wherein the plurality of molecular weight fractions includes a PMLA fraction having a number-averaged molecular weight of 100,000 Da.

4. The method according to claim 3, wherein the PMLA fraction characterized by the number-averaged molecular weight of 100,000 Da comprises 30-40% of the PMLA in the culture broth.

5. The method according to claim 1 further comprising, prior to isolating, determining a PMLA content in the broth by a Hydroxamate/Fe(III)-color assay and terminating the culture at a reading of $A_{540}$ of 1.0 obtained for a 160 microliter sample.

6. The method according to claim 5 wherein terminating comprises adjusting the pH of the culture broth to about 7.5 and cooling the broth to about 10° C.

7. The method according to claim 1 further comprising removing endotoxins and agglutinins by mixing the PMLA with a buffer containing detergent Triton.

8. The method according to claim 7 further comprising incubating a mixture of the PMLA and the Triton, chilling the mixture, thereby obtaining a first phase containing endotoxins and agglutinins, and a second phase containing the PMLA.

9. The method according to claim 8 further comprising collecting the PMLA and removing the residual Triton from the mixture by ion exchange column chromatography.

10. The method according to claim 1 further comprising detecting unbranched PMLA in a plurality of PMLA samples by a quantitative malic acid detection assay and selecting a sample comprising the unbranched PMLA.

11. A method for producing a polymalic acid (PMLA) comprising:
    culturing in a bioreactor *Physarum polycephalum* strain M3CVII in culture medium supplemented with D-glucose and $CaCO_3$ less than about 75 hours;
    separating plasmodia from culture broth, purifying the PMLA from the broth by anion exchange chromatography, obtaining PMLA fractions, precipitating the PMLA from the fractions with ethanol and dissolving the precipitated PMLA in aqueous solution; and,
    fractionating the aqueous solution by gel permeation chromatography, collecting and pooling high purity PMLA fractions characterized by a number-averaged molecular weight of about 100,000 Da.

12. A method for producing a polymalic acid (PMLA) wherein improvements comprise:
    culturing in a bioreactor a *Physarum polycephalum* strain that produces the PMLA wherein the strain is at least one strain selected from: MC3CVII, MC3CVIII, CH813xLU861, LU688, OX110xRA271, LU897xLU898 and LU887; and,
    isolating and purifying the PMLA by gel permeation chromatography and collecting the high purity PMLA fractions, wherein a PMLA fraction pool characterized by a number-averaged molecular weight of about 100,000 Da comprises 30-40% of the PMLA in the culture broth.

13. A method for producing a polymalic acid (PMLA) comprising:
    culturing in a bioreactor a *Physarum polycephalum* strain that produces the PMLA wherein the strain is at least one strain selected from: M3CVIII, CH813xLU861, LU688, OX110xRA271, LU897xLU898, LU887; and,
    isolating and purifying the PMLA from bioreactor culture broth.

14. The method according to claim 13 further comprising activating at least one pendant carboxylic group of the PMLA and conjugating the activated carboxylic group of the PMLA with a pharmaceutically active compound.

* * * * *